(12) United States Patent
Parmentier et al.

(10) Patent No.: US 6,383,972 B1
(45) Date of Patent: May 7, 2002

(54) PREPARATION OF A CATALYST SUPPORT IN ACTIVATED CARBON FIBRES

(75) Inventors: Philippe Parmentier; Jean-Pierre Joly, both of Villeurbanne; Alain Perrard, Sainte-Foy-lès-Lyon, all of (FR)

(73) Assignee: Messier-Bugatti, Velizy Villacoublay (FR)

( * ) Notice: Subject to any disclaimer, the term of this patent is extended or adjusted under 35 U.S.C. 154(b) by 0 days.

(21) Appl. No.: 09/555,037
(22) PCT Filed: Nov. 24, 1998
(86) PCT No.: PCT/FR98/02506
§ 371 Date: May 23, 2000
§ 102(e) Date: May 23, 2000
(87) PCT Pub. No.: WO99/26721
PCT Pub. Date: Jun. 3, 1999

(30) Foreign Application Priority Data

Nov. 24, 1997 (FR) ............................................. 97 14704

(51) Int. Cl.⁷ ................................................. B01J 21/18
(52) U.S. Cl. ........................ 502/180; 502/178; 502/185; 502/325
(58) Field of Search .................................. 502/159, 325, 502/180, 150, 152, 178, 506, 507, 182, 185; 423/22; 252/8.86; 442/61, 165

(56) References Cited

U.S. PATENT DOCUMENTS

| | | | | |
|---|---|---|---|---|
| 4,600,571 A | * | 7/1986 | McCarroll et al. | 423/363 |
| 4,900,618 A | * | 2/1990 | O'Connor et al. | 428/328 |
| 5,169,616 A | * | 12/1992 | Ross | 423/447 |
| 5,741,596 A | * | 4/1998 | Skowronski et al. | 428/457 |
| 5,907,051 A | * | 5/1999 | Matsuda et al. | 558/270 |

FOREIGN PATENT DOCUMENTS

| | | |
|---|---|---|
| DE | 195 25 190 A | 1/1997 |
| EP | 0 299 637 A | 1/1989 |
| EP | 0 779 100 A | 6/1997 |
| FR | 2 521 873 A | 8/1983 |

* cited by examiner

Primary Examiner—Steven P. Griffin
Assistant Examiner—Edward M. Johnson
(74) Attorney, Agent, or Firm—Weingarten, Schurgin, Gagnebin & Lebovici LLP

(57) ABSTRACT

A carbon fiber fabric having large specific surface area is made using a rayon precursor, and a catalyst is fixed on the fabric by impregnation or by cationic exchange. The carbon fiber fabric has pores with a mean size lying in the range 0.3 nm to 3 nm, a carbon content greater than 99%, and a high density of functional groups per unit area which favors the dispersion of metal catalyst in the form of fine particles and which is good for highly selective catalytic reactions in fine chemistry.

25 Claims, 2 Drawing Sheets

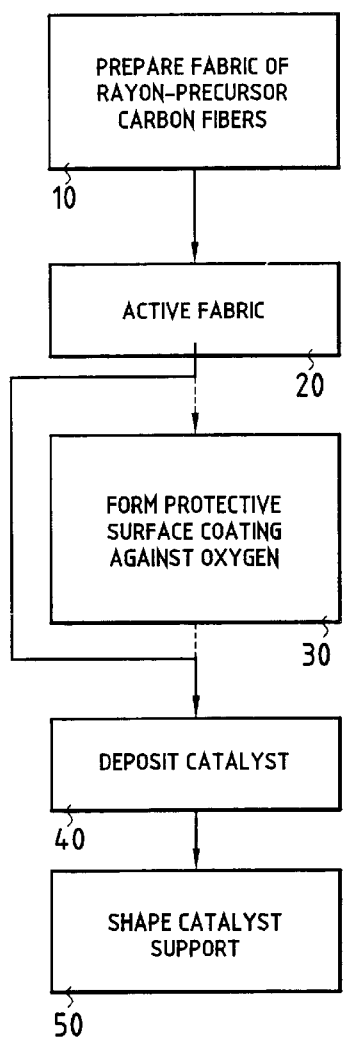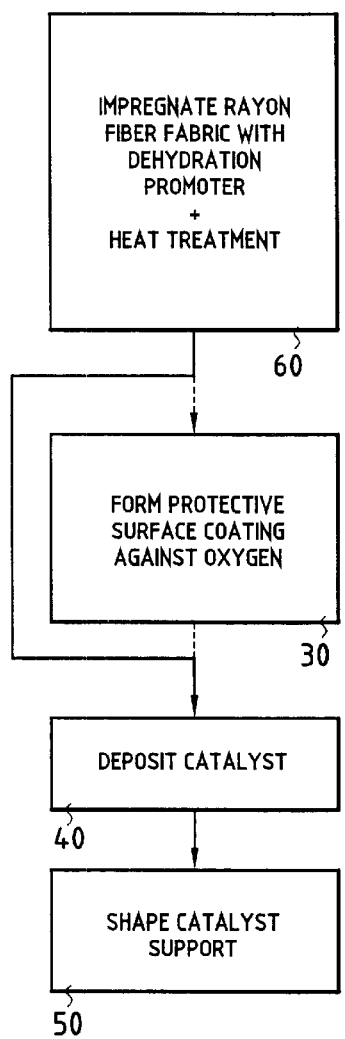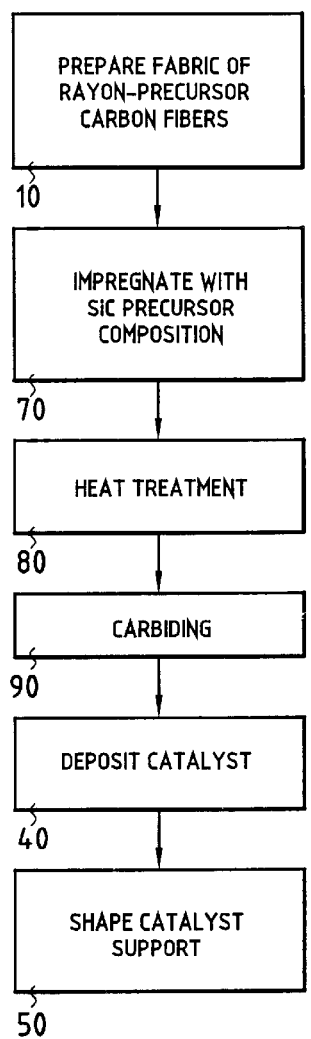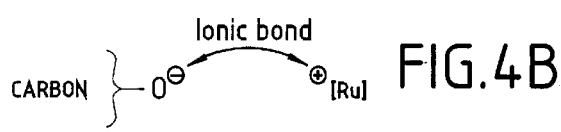

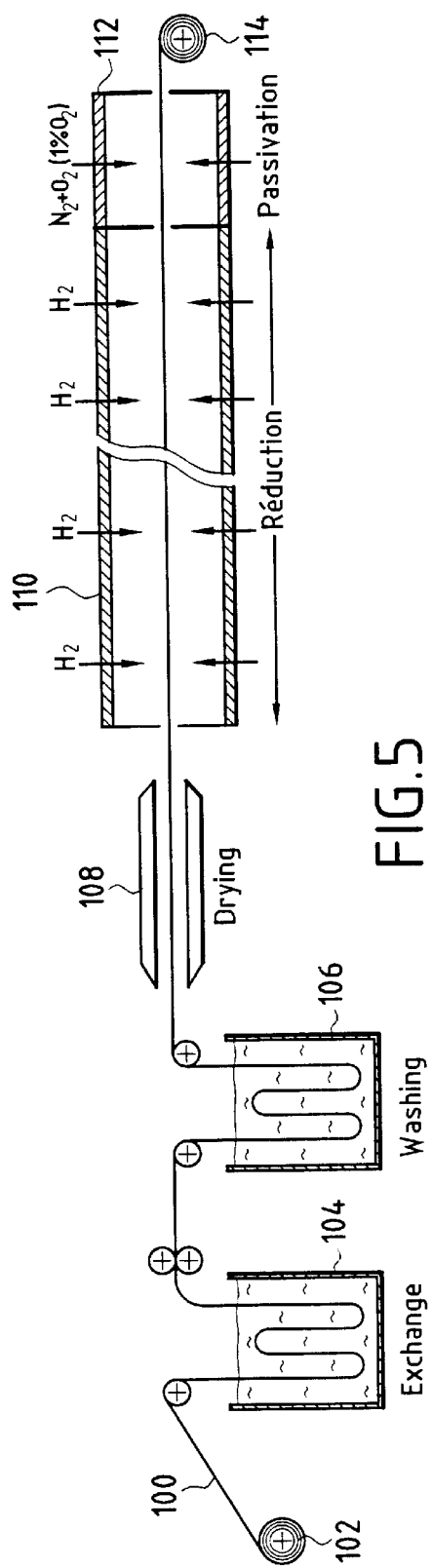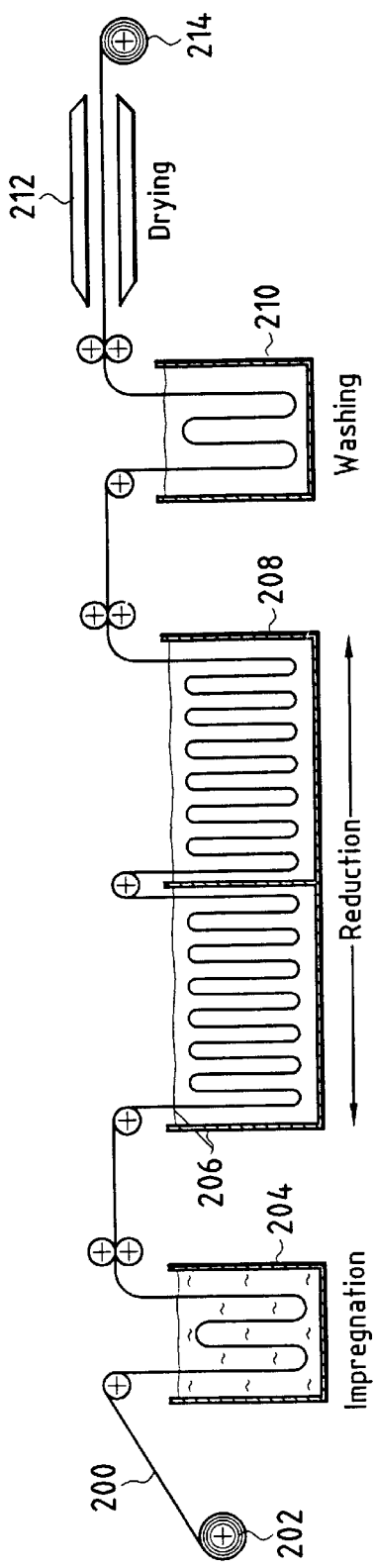

PREPARATION OF A CATALYST SUPPORT IN ACTIVATED CARBON FIBRES

FIELD OF THE INVENTION

The present invention relates to catalyst supports of activated carbon, and more particularly catalyst supports comprising a substrate of activated carbon fibers.

BACKGROUND OF THE INVENTION

In the chemical industry, it is common practice to use catalysts deposited in a finely divided state on substrates.

The substrates used are frequently activated carbons in the form of grains, powders, or extrusions. Their use poses a certain number of problems: micropores that are sometimes difficult of access; the need to sort grain sizes by screening; filtering to eliminate fines; and the risk of grains that are piled up in a reactor becoming crushed; which lead to precursors being selected that give rise to hard carbons (coconuts, olive-stones), but that do not always give good porosity, and that have the potential to create paths for liquids through a bed of carbon grains which leads to the available surfaces not being used to the full.

Proposals have been made for catalyst supports that do not rely on grains, but on carbon fibers of high specific area.

Fibers of small diameter offer a larger exchange area per unit mass of support. In addition, they can be disposed in the form of organized fabrics.

Thus, document FR 2 521 873 A discloses the use of a felt of active carbon or of activated carbon on which a metal catalyst can be deposited such as ruthenium or an association of ruthenium and palladium, and the resulting catalyst support is intended for use in catalytic conversion of glucose into sorbitol. Reference could also be made to document EP 0 299 637 A1 which discloses a support for a metal catalyst, the support being made of a woven cloth of carbon fibers having high specific area, about 1200 square meters per gram ($m^2/g$). Before the catalyst is fixed, the cloth is washed in an acid solution and then rinsed. Such treatments carry a penalty in terms of time and cost of preparing catalyst supports, and the same applies to the oxidation treatments which are frequently performed on activated carbon substrates to augment the density of active sites per unit area prior to fixing the catalyst.

OBJECT AND BRIEF SUMMARY OF THE INVENTION

An object of the invention is to provide a simple method of preparing catalyst supports comprising a substrate of activated carbon fibers and particularly suited for use in fine chemical catalytic reactions that require a high degree of selectivity.

According to the invention, a method of preparing a catalyst support comprising making a carbon fiber fabric having high specific surface area and fixing a catalyst on the fabric is characterized by the fact that a rayon-precursor carbon fiber fabric is used.

In a first implementation of the method, the making of the carbon fiber fabric having high specific area comprises:

carbonizing a rayon fabric which, during a final stage, is-made at a temperature lying in the range 1000° C. to 1300° C., for a duration lying in the range 0.7 minutes (min) to 1.3 min; and the carbonized rayon texture is activated.

Advantageously, the carbonization of the rayon fabric includes the stage of precarbonization performed at a temperature lying in the range 350° C. to 420° C., and the activation is performed at a temperature, lying in the range 850° C. to 950° C., e.g. under an atmosphere of carbon dioxide.

In a second implementation of the method, the making of the carbon fiber fabric having high specific surface area comprises:

impregnating a rayon fabric with a composition containing at least one inorganic ingredient having a function for promoting dehydration of the rayon; and performing heat treatment at a temperature lying in the range 350° C. to 500° C. The impregnating composition can contain an ingredient selected from phosphoric acid, zinc chloride, potassium sulfate, potassium hydroxide, diammonium phosphate, and ammonium chloride.

Advantageously, the heat treatment comprises raising the temperature at a rate lying in the range 1° C./min to 15° C./min followed by a pause at a temperature lying in the range 350° C. to 500° C.

Both the first and the second implementations of the method make it possible to obtain a carbon fiber fabric having a specific area greater than 800 $m^2/g$, and even greater than 1200 $m^2/g$.

In addition to the possibility of obtaining large specific surface area, the use of rayon-precursor carbon fibers provides other particularly significant advantages. Thus, such fibers present a microstructure that favors the formation of surface functions or "active sites" and consequently favors catalyst fixing without necessarily requiring special surface oxidation as is usually the: case with grains of active carbon.

In addition, rayon-precursor carbon fibers, once activated, can present pores with a mean size lying in the range 0.3 nanometers (nm) to 3 nm for filaments with a diameter lying in the range about 5 micrometers ($\mu$m) to about 20 $\mu$m, and with a total porosity of 30% to 50% by volume. This favors great dispersion of the catalyst in the form of fine particles of a size not exceeding 3 nm, thereby obtaining high efficiency during catalytic reactions.

Another advantage consists in the high purity of the resulting carbon fibers: a carbon content greater than 99%, an ash content less than 0.3%, and an alkaline impurity content of less than 1500 parts per million (ppm). Thus, acid washing treatment prior to catalyst fixing is not necessary. In-addition, fibers make it possible to form substrates that are particularly suitable for receiving metal catalysts such as, in particular, ruthenium, platinum, rhenium, palladium, iridium, nickel, . . . or a combination of such metals, for uses in the field of fine chemistry, the purity of the carbon support being favorable to conferring the necessary selectivity. Furthermore, carbon derived from a rayon precursor is hydrophilic and consequently favors exchange with liquids, in particular aqueous media.

When the catalyst support is used in an oxidizing medium at a temperature higher than the temperature at which the carbon begins to oxidize, it is advantageous to provide the activated carbon fibers with a coating for protecting them against oxidation, e.g. a skin of silicon carbide. This can be formed by reacting the carbon of the fibers with silicon and/or a silicon compound such as silica.

In yet another implementation of the invention, the making of the carbon fiber fabric having high specific surface area comprises:

carbonizing a rayon fabric;

impregnating the carbonized fabric with a composition containing a precursor of a material for protection against oxidation; and heat treatment for transforming the precursor so as to form a coating for protection against oxidation on the surface of the carbon fibers, the resulting fabric having a specific surface area that can be greater than 10 m$^2$/g and can be as much as a few tens of m$^2$/g, enabling the catalysts used to be deposited in an oxidizing medium.

Various known methods of fixing the catalyst to the activated carbon fiber fabric can be used, such as cationic exchange or liquid impregnation. They are advantageously performed continuously by causing the fabric to travel through one or more baths.

The carbon fiber fabric is essentially a two-dimensional fabric which is shaped after the catalyst has been fixed so as to ensure that the catalyst is distributed in substantially uniform manner throughout the support. This shaping is performed so as to make a support that matches the volume of a reactor to be occupied. For example, it can comprise operations of rolling, winding, or indeed needling plies so as to impart cohesion to the shaped support.

BRIEF DESCRIPTION OF THE DRAWINGS

The following description that is given by way of non-limiting indication refers to the accompanying drawings, in which:

FIG. 1 shows the successive steps in preparing a catalyst support in a first implementation of the invention;

FIG. 2 shows the successive steps in preparing a catalyst support in a second implementation of the invention;

FIG. 3 shows the successive steps in preparing a catalyst support in a third implementation of the invention;

FIGS. 4A and 4B illustrate in highly diagrammatic manner a process of cation exchange;

FIG. 5 is a diagram of a continuous process for fixing a catalyst on a cloth by impregnation; and FIG. 6 is a diagram of a continuous process for fixing a catalyst on a cloth by impregnation.

DESCRIPTION OF PREFERRED IMPLEMENTATIONS

A first implementation of a method of the invention is given in FIG. 1. A first step 10 consists in preparing a carbon fiber fabric in the form of a woven cloth, a knit, a braid, a felt, a single-direction sheet, a plurality of superposed single-direction sheets, preferably extending in different directions and bonded together by light needling, or any other analogous fabric that is essentially two-dimensional.

The carbon fiber fabric is obtained directly from carbon threads or fibers derived from rayon threads or fibers by heat treatment or preferably from a fabric of rayon threads or fibers, with the heat treatment for transforming the rayon then being performed after the fabric has been made up.

Heat treatment for transforming rayon into carbon comprises a precarbonization stage at a temperature lying in the range 350° C. to 420° C., and preferably at around 400° C., followed by a final carbonization stage at a temperature lying in the range 1000° C. to 1300° C., and preferably at about 1200° C., under an atmosphere of nitrogen and for a duration lying in the range 0.7 min to 1.3 min. Final carbonization is preferably performed under low pressure, e.g. in the range 5 Pascals (Pa) to 60 Pa, thereby favoring the elimination of impurities entrained with the gas effluents and favoring the migration of alkaline impurities to thee surface of the fibers from which they can be eliminated merely by rinsing in demineralized water, without any need for washing in acid.

This produces carbon fibers of, high purity, with a carbon content greater than 99%, an ash content of less than 0.3%, and an alkaline impurity content of less than 1500 ppm. The fibers obtained are also remarkable in that they are constituted in structural terms by a large number of very small crystallites having a mean height $L_c$ of about 1 nm and a mean width $L_a$ of about 3 nm. These crystallites provide a large number of active sites at the margins of the graphene planes favoring the formation of functional surface groups when the fabric is put back into air after carbonization, without it being necessary to proceed with specific oxidation treatment. Subsequent activation considerably amplifies the density of surface functions per unit area.

Activation (step 20) is performed by subjecting the carbon fiber fabric to heat treatment under an oxidizing atmosphere, such as steam or preferably carbon dioxide or a mixture of carbon dioxide and steam. The heat treatment is preferably performed at a temperature lying in the range 850° C. to 950° C. and its duration preferably lies in the range 50 min to 300 min as a function of the desired specific surface area. It is possible to perform activation continuously by causing the carbon fiber fabric to travel through a heat treatment zone of an oven in which a flow of oxidizing gas is maintained. Such a method is described, for example, in document FR-A-2 741 363.

Activation confers the desired specific surface area and porosity to the fabric. The specific surface area is greater than 800 m$^2$/g and even greater than 1200 m$^2$/g. The porosity is characterized by pores having a mean diameter lying in the range 0.3 nm to 3 nm and overall porosity lying in the range 30% to 50%. This is measured by the known technique of small angle X-ray scattering (the SAXS technique). It consists in exposing the fibers to a beam of X-rays under conditions such that electron density contrast exists between the voids (pores) and the material (carbon), giving an intensity of scattering that is related to the total porosity of the carbon fibers.

An optional third step 30 consists in providing the activated carbon fiber fabric with a surface coating to protect it against oxidation, so as to enable the catalyst support to be used in an oxidizing atmosphere.

By way of example, the surface coating can consist in a skin of silicon carbide (SiC). It can be formed by reaction, by depositing a dispersion of silica ($SiO_2$) alone or of a mixture of silica and silicon (Si), e.g. in the form of a powder in suspension in water, and by performing heat treatment at a temperature, e.g. lying in the range 1300° C. to 1700° C.

A fourth step 40 consists in depositing the catalyst on the resulting activated carbon fiber texture. Because the texture is derived from a rayon precursor, it presents microporosity and a density of functional groups per unit area (active sites) that make it-suitable for fixing-very small particles of a metal catalyst such as ruthenium, platinum, rhenium, palladium, iridium, or nickel in particular, or other metals or combinations of metals known as catalysts for applications in the field of fine chemistry. Rayon-precursor carbon fibers present a residual oxygen content that favors the presence of active sites and that does not require surface oxidation treatment for this purpose. The resulting density per unit area of surface functional groups is therefore high. Surface chemistry, as characterized by Boehm's method, gives rise to acid functional groups at a concentration of 0.3 millimole per gram (meq/g) to 0.8 meq/g, of which 0.02 meq/g to 0.06 meq/g are carboxylic functions.

The catalyst can be deposited by cationic exchange or by liquid impregnation, with implementations of such processes being described below. The porosity and surface chemistry characteristics enable a metal catalyst to be dispersed in the form of fine particles of mean size lying in the range about 1 nm to 3 nm with a dispersion ratio that is exceptionally high, lying in the range 0.3 to 0.7. Dispersion ratio represents the number of metal atoms on the surface divided by the total number of metal atoms. It is measured by hydrogen chemisorption.

A final step 50 consists in shaping the catalyst support, e.g. to match it to the volume that it is to occupy inside a reactor.

Shaping can be performed by rolling or winding the activated fabric on which the catalyst is fixed, or by superposing plies cut out from said fabric. In which case, the plies can be bonded together by needling.

FIG. 2 shows a second implementation of a method of the invention, which differs from the first implementation in that steps 10 and 20 of obtaining an activated carbon fiber texture are replaced by a step 60, while the following steps 30 to 50 remain unchanged.

Step 60 consists in starting from a rayon fiber fabric and in impregnating it with a composition that, after carbonization, serves to obtain an activated carbon fiber texture directly.

Impregnation is performed using a composition containing an inorganic ingredient that promotes dehydration of rayon, such as an ingredient selected from phosphoric acid, zinc chloride, potassium sulfate, potassium hydroxide, diammonium phosphate, and ammonium chloride. Impregnation is preferably performed by means of a composition containing phosphoric acid so that the mass of acid fixed on the fabric lies in the range 10% to 22% of the mass of dry fabric. The heat treatment comprises raising temperature at a rate lying in the range 1° C./min to 15° C./min followed by a pause that is preferably performed at a temperature lying in the range 350° C. to 500° C. under an inert atmosphere or an atmosphere containing a reaction activator such as carbon dioxide or steam. The texture is then preferably washed. Such a method is described in international patent application No. WO 98/41678 in the name of the Applicant.

A carbon fiber fabric having high specific surface area is obtained with characteristics of purity, porosity, and surface active sites that are similar to the fabric obtained using steps 10 and 20 of the method described with reference to FIG. 1, i.e. a fabric that is particularly suitable for use as a catalyst support for catalytic reactions in the field of fine chemistry.

FIG. 3 shows a third implementation of a method of the invention enabling a catalyst support to be obtained in which the carbon fibers are coated in silicon carbide for use in an oxidizing medium.

A first step 10 consists in making a carbon fiber fabric as described with reference to FIG. 1. The resulting rayon-precursor carbon fibers have structural disorganization that is good for obtaining fibers having a core of carbon, a skin of silicon carbide (SiC), and high specific surface area by using the following process.

A second step 70 consists in impregnating the carbon fiber fabric with a sol-gel of an SiC precursor in a mixture of ethanol, water, and hydrochloric acid. By way of example, the precursor is an ethyl silicate such as tetraethoxysilane. (TEOS).

Thereafter (step 80), heat treatment is performed at a temperature of about 900° C. under argon, leaving a film of silica on the carbon fibers.

The silica is transformed into silicon carbide by carbiding heat treatment at a temperature of about 1550° C. under argon (step 90).

This method makes it possible to coat the carbon fibers in a thin film of SiC that is protective against oxidation without consuming the carbon of the fibers to form the SiC coating, and thus without affecting the mechanical properties of the fabric. In addition, the fabric as finally obtained presents relatively high specific surface area, about 20 $m^2/g$, which together with its SiC coating makes it an excellent candidate as a support for a catalyst in an oxidizing medium at high temperature. Steps 40 and 50 of depositing the catalyst and shaping the support can then be performed in the same manner as in the other implementations of the method.

EXAMPLES

Two particular implementations of the invention for making ruthenium supports are described below by way of illustration.

Example 1

Cationic Exchange

A woven rayon cloth was used made up of a multifilament viscose obtained from 190 tex threads woven in a 15×15 set (15 threads per cm in both the warp and the weft directions).

After de-oiling, the cloth was carbonized by being raised to a temperature of about 400° C. for about 12 hours (h), and then to a final temperature of about 1200° C. for about 1 min under nitrogen at a pressure of 30 Pa. The resulting carbon cloth was activated by making the cloth travel through a heat treatment zone of an oven in an atmosphere constituted by 100% carbon dioxide. This zone was implemented, as were the zones for raising and lowering the temperature, by a muffle in the form of a tunnel through which the cloth was advanced continuously. The heat treatment was performed at a temperature of about 920° C. and the time spent at that temperature was about 1 h.

The resulting activated carbon cloth had micropores with a mean size equal to about 0.6 nm, overall porosity of 40% (relative to the apparent volume of the cloth), and a carbon content of 99%.

A sample of the activated carbon cloth having an initial mass of 11.06 g was held in suspension by stirring in 100 milliliters (ml) of 1N ammonia through which nitrogen was bubbled. 30 ml of a molar ammoniacal solution in which amass of 0.44 g of the ruthenium salt $Ru(NH_3)_6Cl_3$ had been dissolved was added slowly. The system was allowed to come to equilibrium over a period of 1 h. In the ammonia medium, protons are taken from the anchor sites in the manner shown in FIG. 4A, thus favoring the formation of an ionic bond with the metal salt of the Ru $(NH_3)_6^{3+}Cl^-$ type as shown in FIG. 4B. Once the metal had been strongly fixed to the surface of the support by ionic bonding, the cloth was washed in water until the mother liquid was neutral.

The cloth could then be dried under nitrogen at about 120° C. prior to the ruthenium being reduced at about 250° C. under a flow of 4 liters per hour (l/h) to 6 l/h of hydrogen $H_2$. Temperature was raised at 2° C./min with a pause of 3.5 h at 250° C. The reduced catalyst was cooled to ambient temperature under $H_2$.

Prior to being put back into air, the catalyst was passivated so as to prevent any in depth oxidation of the metal. Passivation was performed at 25° C. under a flow of 6 liters per hour (l/h) of a mixture of oxygen $O_2$ and of nitrogen $N_2$ in which the volume percentage of oxygen was equal to 1%.

At the end of those operations, 12.6 g of carbon cloth in good condition was recovered carrying 0.5% by weight of fixed ruthenium, the ruthenium being in the form of particles having a mean size equal to about 1 nm and having a dispersion ratio of about 0.7.

The above-described process of fixing ruthenium by cationic exchange can advantageously be performed continuously by using an installation of the kind shown diagrammatically in FIG. 5.

The activated carbon fiber cloth 100 is paid out continuously from a storage roll 102. It passes along a zigzag path through a bath 104 containing ammonia and a dissolved mass of the salt $Ru(NH_3)_6Cl_3$ in a molar ratio of 1 to 0.01, respectively, with nitrogen being bubbled through.

On leaving the bath 104, the cloth is directed to a washing bath 106 containing demineralized water.

On leaving the bath 106, the cloth is dried by passing through a tunnel 108 at a temperature of about 120° C. under nitrogen, and it is then admitted into a hydrogenation oven 110 where the ruthenium is reduced.

On leaving the oven 110, the cloth passes into a passivation compartment 112 where it is passivated under a mixture of nitrogen and oxygen (with an $O_2$ content of 1% by volume), prior to being taken upon a storage reel 114.

The lengths of the paths followed by the cloth through the baths 104 and 106 and the travel speed are selected so: as to ensure that the cloth spends 1 h and 30 min approximately in the baths 104 and 106 respectively.

Heating in the oven 110 and the length thereof are selected relative to the travel speed of the cloth so as to comply with the rate of temperature rise and the duration of the pause at high temperature required for reducing ruthenium.

Although the above description relates to ruthenium, the process of fixing a metal catalyst M by cationic exchange can be used with metals other than ruthenium and capable of being presented in the form of a cationic salt of the type $[M(NH_3)_x]^{y+}$, $yCl^-$, e.g. platinum.

Example 2

Liquid Impregnation

A sample of activated carbon cloth obtained as in Example 1 and having an initial mass of 6.2 g was put into suspension at ambient-temperature in 300 ml of demineralized water through which nitrogen was bubbled. 25 ml of a molar hydrochloric solution containing 0.3 g of $RuCl_3xH_2O$ was added slowly and impregnation was allowed to take place over 30 min.

Thereafter, the ruthenium was reduced at 0° C. and under an inert atmosphere, by adding an excess of 75 ml of formol at 37% and then 40 ml of potassium hydroxide at 30%, giving a molar ratio of HCHO/KOH equal to 3. After about 10 h, the cloth was washed for about 1 h in demineralized water and then dried at about 120° C. under nitrogen.

6.92 g of carbon cloth were obtained in good condition carrying 0.83% by weight of fixed ruthenium. The ruthenium was in the form of particles having a mean size of about 2 nm and the dispersion ratio was about 0.5.

The above-described process of fixing ruthenium by impregnation can advantageously be performed continuously by using an installation of the kind shown diagrammatically in FIG. 6.

The activated carbon fiber cloth 200 is continuously delivered from a storage roll 202. It travels at ambient temperature along a zigzag path through a bath 204 containing a molar hydrochloric solution of $RuCl_3xH_2O$ having 1 mole of HCl for $4 \times 10^3$ moles of $RuCl_3$.

The impregnated cloth is reduced by traveling at ambient temperature through two consecutive baths 206 and 208 containing formol at 37% and potassium hydroxide at 30%, and following two zigzag paths.

The travel speed of the cloth and the lengths of the paths in the baths, 204, 206, and 208 are selected so as to have impregnation with a duration of about 30 min and reduction with a total duration of about 10 h.

On leaving the bath 208, the cloth is admitted into a bath 210 to be washed in demineralized water for about 1 h.

It is dried by passing through a tunnel 212 and is then taken up on a storage reel 214. The method can be used for other metal catalysts M, by using the corresponding anionic complex $MCl_x$ in an acid medium.

Comparative Test (Hydrogenation of Glucose)

A 30% by weight aqueous solution of glucose was hydrogenated in a stirred autoclave at 100° C. under 80 bars of hydrogen ($H_2$) in the presence of ruthenium fixed on activated carbon cloths obtained as in Example 1 (TCA1) and Example 2 (TCA2). By way of comparison, the same reaction was performed under the same conditions, with the exception of the catalyst support which was constituted by grains of active carbon on which 1.2% by weight of ruthenium had been fixed (Ru/AC). That is a catalyst support known in the state of the art as having good performance.

The effectiveness of the catalyst supports was estimated on the bases of glucose conversion rate C, of sorbitol selectivity S, and of initial specific activity $A_s$ (number of moles of glucose converted per hour and per gram of ruthenium). The table below gives the results obtained.

|   | Ru/AC | TCA1 | TCA2 |
| --- | --- | --- | --- |
| S | 99.3% | 99.8% | 99.5% |
| C | 83% | 98% | 99.7% |
| $A_s$ | 2500 mmol/h/g | 2000 mmol/h/g | 2500 mmol/h/g |

The catalytic properties obtained with catalyst supports TCA1 and TCA2 are comparable to those with the Ru/AC control. It can be seen that glucose was converted almost completely (not less than 98%), and that sorbitol selectivity was excellent (greater than 99%), while conserving initial specific activities similar to those obtained in the state of the art. In-addition, the post-reaction separation stages were simplified, in particular because of the absence of any fine particles of the kind usually encountered with catalyst supports using grains of activated carbon.

The catalyst support of the invention is particularly remarkable for the great selectivity it makes possible, and it is therefore particularly advantageous for applications in the fine chemistry field.

What is claimed is:

1. A method of preparing a catalyst support comprising making a rayon-precursor activated carbon fiber fabric and fixing a catalyst on the fabric, the method being characterized in that:

making the activated carbon fiber fabric includes a stage of precarbonizing a rayon fiber fabric at a temperature in the range of 350° C. to 420° C. followed by a stage of final carbonization at a temperature in the range of 1000° C. to 1300° C., for a duration in the range of 0.7 min to 1.3 min, and of activation at a temperature in the range of 850° C. to 950° C., so that an activated carbon fiber fabric is obtained having pores with a mean size in the range of 0.3 nm to 3 nm, a carbon content greater than 99%, an ash content less than 0.3%, and an alkaline impurity content of less than 1500 ppm, and fixing the catalyst is performed by one of the following two methods: by impregnating the activated carbon fiber fabric with a composition containing a compound of the catalyst to be fixed; and by cationic exchange by immersing the activated carbon cloth in a bath containing a solution of a salt of the catalyst to be fixed.

2. A method according to claim 1, characterized in that the activation is performed under an atmosphere of carbon dioxide.

3. A method according to claim 2, characterized in that:

the carbon fiber fabric has a specific surface area of not less than 1200 m²/g;

a fabric is made of activated carbon presenting acid functional surface groups at a concentration of 0.3 meq/g to 0.8 meq/g;

the functional groups comprise 0.02 meq/g to 0.06 meq/g of carboxylic functions;

the method further comprising the step of forming a protective silicon carbide coating against surface oxidation of the carbon fibers.

4. A method according to claim 3, characterized in that the catalyst is fixed by causing the carbon fiber fabric to travel continuously through at least one bath;

the carbon fiber fabric is a woven cloth;

the catalyst support is shaped after the catalyst has been fixed; and shaping the catalyst support includes a step of needling.

5. A method according to claim 1, characterized in that the carbon fiber fabric has a specific surface area of not less than 800 m²/g.

6. A method according to claim 5, characterized in that the carbon fiber fabric has a specific surface area of not less than 1200 m²/g.

7. A method according to claim 1, characterized in that a fabric is made of activated carbon presenting acid functional surface groups at a concentration of 0.3 meq/g to 0.8 meq/g.

8. A method according to claim 7, characterized in that the functional groups comprise 0.02 meq/g to 0.06 meq/g of carboxylic functions.

9. A method according to claim 1, characterized in that it further comprises forming a protective coating against surface oxidation of the carbon fibers.

10. A method according to claim 1, characterized in that a silicon carbide coating is formed.

11. A method according to claim 1, characterized in that the making of the carbon fiber fabric having high specific surface area comprises:

carbonizing a rayon fabric;

impregnating the carbonized fabric with a composition containing a precursor of a material for protection against oxidation; and transforming the precursor with heat treatment so as to form a coating for protection against oxidation on the surface of the carbon fibers.

12. A method according to claim 11, characterized in that the carbon fiber fabric coated in a coating for protection against oxidation has a specific surface area greater than 10 m²/g.

13. A method according to claim 12, characterized in that the catalyst is fixed by causing the carbon fiber fabric to travel continuously through at least one bath;

the carbon fiber fabric is a woven cloth;

the catalyst support is shaped after the catalyst has been fixed; and shaping the catalyst support includes a step of needling.

14. A method according to claim 1, characterized in that the catalyst is fixed by causing the carbon fiber fabric to travel continuously through at least one bath.

15. A method according to claim 1, characterized in that the carbon fiber fabric is a woven cloth.

16. A method according to claim 1, characterized in that the catalyst support is shaped after the catalyst has been fixed.

17. A method according to claim 16, characterized in that shaping the catalyst support includes a step of needling.

18. A catalyst support comprising a rayon-precursor activated carbon fiber fabric and a metal catalyst fixed on the fibers, the support being characterized in that:

the activated carbon fiber fabric has pores with a mean size in the range of 0.3 nm to 3 nm, a carbon content greater than 99%, an ash content less than 0.3%, and an alkaline impurity content of less than 1500 ppm, and the catalyst is in the form of particles having a mean size in the range of 1 nm to 3 nm.

19. A catalyst support according to claim 18, wherein said catalyst has a dispersion ratio in the range of 0.3 to 0.7.

20. A catalyst support according to claim 18, characterized in that the catalyst is ruthenium.

21. A catalyst support according to claim 20, characterized in that the ruthenium is not less than 0.5% of a total mass of the support.

22. A catalyst support according to claim 20, characterized in that:

the mass of fixed ruthenium is not less than 0.5% of the total mass of the support;

the carbon fiber fabric is a woven cloth; and the carbon fibers of the fabric are provided with a silicon carbide coating for protecting the carbon fibers against oxidation.

23. A catalyst support according to claim 18, characterized in that the carbon fiber fabric is a woven cloth.

24. A catalyst support according to claim 18, characterized in that the carbon fibers of the fabric are provided with a coating for protecting the carbon fibers against oxidation.

25. A catalyst support according to claim 24, characterized in that the coating is a silicon carbide.

* * * * *

UNITED STATES PATENT AND TRADEMARK OFFICE
CERTIFICATE OF CORRECTION

PATENT NO. : 6,383,972 B1  Page 1 of 1
DATED : May 7, 2002
INVENTOR(S) : Philippe Parmentier et al.

It is certified that error appears in the above-identified patent and that said Letters Patent is hereby corrected as shown below:

Column 1,
Line 62, "is-made" should read -- is made --;

Column 2,
Line 2, "temperature,lying" should read -- temperature lying --;
Line 31, "the:case" should read -- the case --;

Column 3,
Line 64, "thee surface" should read -- the surface --;

Column 4,
Line 1, "of, high" should read -- of high --;
Line 52, "it-suitable" should read -- it suitable --;
Line 52, "fixing-very" should read -- fixing very --;

Column 6,
Line 49, "amass" should read -- a mass --;

Column 7,
Line 26, "so:" should read -- so --; and
Line 44, "ambient-temperature" should read -- ambient temperature --.

Signed and Sealed this

Eleventh Day of March, 2003

JAMES E. ROGAN
*Director of the United States Patent and Trademark Office*